(12) United States Patent
France

(10) Patent No.: US 7,560,115 B1
(45) Date of Patent: Jul. 14, 2009

(54) METHODS AND COMPOSITIONS FOR TREATING HOT FLASHES

(76) Inventor: Melissa France, 11574 W. 106th Way, Westminster, CO (US) 80021

( * ) Notice: Subject to any disclaimer, the term of this patent is extended or adjusted under 35 U.S.C. 154(b) by 0 days.

(21) Appl. No.: 12/154,608

(22) Filed: May 22, 2008

(51) Int. Cl.
*A61K 36/05* (2006.01)
(52) U.S. Cl. .................................. 424/195.17
(58) Field of Classification Search ........... None
See application file for complete search history.

(56) References Cited

OTHER PUBLICATIONS http://www.ucmp.berkeley.edu/greenalgae/greenalgae.html—accessed Oct. 2008.*

\* cited by examiner

*Primary Examiner*—Susan C Hoffman
(74) *Attorney, Agent, or Firm*—Russo & Duckworth, LLP

(57) ABSTRACT

Hot flashes are treated by topical application of a treatment composition including an extract of a green marine algae. A preferred green marine algae is *Enteromorpha compressa*.

2 Claims, No Drawings

METHODS AND COMPOSITIONS FOR TREATING HOT FLASHES

BACKGROUND OF THE INVENTION

This invention relates to methods for treating hot flashes. According to another aspect, the invention pertains to compositions useful in treating hot flashes.

Hot flashes are mostly caused by the hormonal changes of menopause, but can also be affected by lifestyle and medications. A diminished level of estrogen has a direct effect on the hypothalamus, the part of the brain responsible for controlling appetite, sleep cycles, sex hormones, and body temperature. The drop in estrogen confuses the hypothalamus—which is sometimes referred to as the body's "thermostat"—and makes it read "too hot."

The brain responds to this report by broadcasting an alert to the heart, blood vessels, and nervous system to get rid of the heat. The message is instantly transmitted by the nervous system's chemical messenger, epinephrine, and related compounds: norepinephrine, prostaglandin, serotonin. The heart pumps faster, the blood vessels dilate to circulate more blood to radiate more heat, and the perspiration glands release perspiration to cool the body off even more.

This heat-releasing mechanism is how the body prevents overheating in the summer. But, when the process is triggered instead by a drop in estrogen, the brain's confused response can make the person very uncomfortable. Some women's skin temperature can rise 6° C. during a hot flash. The body cools down when it shouldn't and perspiration leaves the person soaking wet.

Eighty-five percent of the women in the United States experience hot flashes of some kind as they approach menopause and for the first year or two after their menstrual periods stop. Between 20 and 50% of women continue to have them for many more years. As time goes on, the intensity decreases.

There is considerable variation in time of onset, duration, frequency, and the nature of hot flashes. An episode can last a few seconds or a few minutes, occasionally even an hour, but it can take another half hour for the person to feel well again. The most common time of onset is between six and eight in the morning, and between six to ten at night.

Most women have mild to moderate hot flashes, but about 10-15% of women experience such severe hot flashes that they seek medical attention. The faster the person goes through the transition from regular periods to no periods—the peri-menopause or climacteric—the more significant the hot flashes will be.

Women experiencing hot flashes may encounter a variety of symptoms, including a feeling of mild warmth to intense heat spreading through the upper body and face, a flushed appearance with red, blotchy skin on the face, neck and upper chest, rapid heartbeat, perspiration (mostly on the upper body) and a chilled feeling as the hot flash subsides.

Aside from obvious techniques such as wearing light clothing, using a fan, drinking cold drinks, controlled breathing, etc., the prior art has suggested a number of non-prescription dietary supplements to curb hot flashes, such as black cohosh, soy, red clover, and vitamin E. However, none of these have proven effective in clinical trials.

Low doses of some anti-depressants have been shown to decrease hot flashes in some clinical trials, notably selective serotonin reuptake inhibitors and norepinephrine reuptake inhibitors. There are potential side effects from these medications, such as nausea, dizziness, weight gain and sexual dysfunction.

Other prescription medications have provided some relief from hot flashes, such as Gabapentin (Neurotinin) and Clonidine, but, again, side effects such as drowsiness, dizziness, nausea, imbalance, dry mouth and constipation may limit use of the drugs.

Hormone therapies have proven most effective, such as estrogen therapy and progesterone therapy and combinations of estrogen and progesterone. However, there are definite risks to hormone therapy such as increased risk of breast cancer, stroke and heart disease.

Accordingly, it would be highly desirable to provide a treatment for hot flashes which is effective and which does not cause debilitating side effects. In particular, it would be desirable to provide such treatment which can be used simultaneously with hormone therapy, allowing hormone therapy at lower (safer) dose rate and lower (safer) total doses, while providing effective results.

SUMMARY OF THE INVENTION

I have now discovered a method of treating hot flashes of a woman during peri-menopause or menopause, comprising applying to the skin of the woman experiencing hot flash onset or hot flash symptoms a composition comprising an oligosaccharide extract of green marine algae, such as *Uvale (L)* or *enteromorpha (L)*, in a pharmacologically acceptable liquid carrier.

In a preferred embodiment of the invention, the carrier includes water and a humectant which is at least one member selected of the group consisting of glycerine and an alkylene glycol, e.g. propylene glycol or butylene glycol. The quantities of these components will vary with the other components present and the solubilities of the other components, in accordance with art-recognized principles.

The amount of the oligosaccharide extract component varies from about 0.5 to about 10 wt. % of the total composition. The preferred amount is about 4 wt. %, but lower concentrations are at least partly operable and larger concentrations are not harmful.

DETAILED DESCRIPTION OF THE INVENTION

The composition is applied topically to the skin of the woman experiencing hot flash onset or hot flash symptoms. The composition is liberally applied directly to the affected areas of skin, which may include the upper body and face. Application can be made directly by pouring a quantity on the skin and then spreading it by hand to the affected skin area or the composition can be applied by a sponge or pad carrying the composition. Alternatively, application can be effected by spraying the composition from a pressurized container through a finger-actuated spray nozzle. In the presently preferred embodiment, the composition is topically applied from a non-pressurized bottle equipped with a finger-actuated pump. The pump delivers the composition in liquid form to a spray nozzle, which converts the liquid to an aerosol or spray of fine droplets.

The liquid carrier of the composition is aqueous, but may include glycerine and/or butylene glycol as humectants and as co-solvents for the other components of the composition, some of which are water soluble and some of which may be soluble in non-polar solvents. Additionally, glycerine improves the texture and viscosity of the composition after application, providing for even spreading and preventing it from running off the area of skin intended for application.

The green marine algae component of the compositions used in practicing the invention is an extract. Preparation of the extract can be accomplished by a wide variety of techniques which will readily occur to those skilled in the art.

For example, the algae is first washed and blotted dry between sheets of absorbent paper. The dried algae is then crushed in a mortar and pestle with acid-washed sand in the presence of a phosphate buffer saline extractant (0.005M phosphate and 0.15M NaCl, pH=7.4). The resultant crushed algae-sand mixture is centrifuged (Remi R-10) at 10,000 rpm for fifteen minutes at 4° C. The pellet remaining in the centrifuge cup is discarded and the supernatant is then diluted with the phosphate buffer to make a 20 wt. % extract.

Alternatively, the algae is heated in a hot air current and ground to a flour in a Waring blender. The flour is then extracted in a Soxhlet apparatus with acetone (48 hours) and ethanol (48 hours) to remove the pigmentation. The depigmented flour is than sequentially extracted with ammonium oxylate in a sodium acetate buffer (pH=5). The unextracted residue is separated from the liquid using a centrifuge, followed by filtering the centrifugate through a G-3 fritted glass filter. The filtered centrifugate is washed with aqueous ethanol, ethanol and acetone and vacuum dried over $P_2O_5$, to yield a powdered oxylate-soluble extract.

Similar procedures or other standard procedures in the art are employed to provide extracts of other botanicals which may be included in compositions used in accordance with the presently preferred practice of the method of the invention. For example, it may be desirable to include one or more botanical extracts in the compositions used in accordance with the invention. If so, suggested ranges for these extracts are from about 0.0001 to 10%, preferably about 0.0005 to 8%, more preferably about 0.01 to 0.05% by weight of the total composition.

Suitable botanical extracts include extracts from plants (herbs, roots, flowers, fruits, seeds) such as flowers, fruits, vegetables, including acacia (dealbata, framesiana, senegal), acer saccharinum (sugar maple), acidopholus, acorus, aesculus, agaricus, agave, agrimonia, aloe, citrus, brassica, cinnamon, orange, apple, blueberry, cranberry, peach, pear, lemon, lime, pea, seaweed, green tea, chamomile, willowbark, mulberry, poppy, and those set forth on pages 1646 through 1660 of the CTFA Cosmetic Ingredient Handbook, Eighth Edition, Volume 2. Further specific examples include, but are not limited to, Glycyrrhiza Glabra, Salix Nigra, Macrocycstis Pyrifera, Pyrus Malus, Saxifraga Sarmentosa, Vitis Vinifera, Morus Nigra, Scutellaria Baicalensis, Anthemis Nobilis, Salvia Sclarea, Rosmarinus Officianalis, Citrus Medica Limonum, and mixtures thereof. In the presently preferred embodiment of the invention the topically composition includes extracts of grapefruit, cucumber, green tea, bee pollen, orange flower, chamomile, sea kelp and lavender.

The following examples are provided in order to illustrate practice of the invention and to identify the presently preferred embodiments thereof. These examples are only illustrative and are not to be taken as a limitation on the scope of the invention, which is defined only by the appended claims.

The following compositions are formulated. All numbers indicate percent by weight:

EXAMPLE 1

| | |
|---|---|
| purified water | 77.7 |
| glycerine | 11.1 |
| butylene glycol | 11.1 |

EXAMPLE 2

| | |
|---|---|
| purified water | 70.0 |
| glycerine | 10.0 |
| butylene glycol | 10.0 |
| enteromorpha compressa extract | 10.0 |

EXAMPLE 3

Skin temperatures are measured one, five and ten minutes after application by spray from a finger-actuated spray pump container of the compositions of Examples 1 and 2, to the forearms, foreheads, throats and necks of women who are experiencing hot flashes. The skin temperatures of the test subjects are measured at the forehead. The reductions in skin temperatures from the initial temperature are:

| Treatment | Reduction In Skin Temperature at Minutes (° F.) | | |
|---|---|---|---|
| Composition | 1 | 5 | 10 |
| Example 1 | 1.0 | 0.5 | 0 |
| Example 2 | 2.0 | 3.0 | 3.0 |

EXAMPLE 4

The following formulation is prepared to illustrate the composition used in accordance with the presently preferred practice of the method of the invention:

| | % by Weight |
|---|---|
| Purified Water | 91.24 |
| Glycerine | 2.00 |
| Butylene Glycol | 2.00 |
| enteromorpha compressa extract | 4.00 |
| Diazolidinyl urea/Iodopropynyl butyl carbamate (preservative) | 0.40 |
| Polysorbate 80 (nonionic surfactant) | 0.30 |
| Fragrance | 0.05 |
| Botanical extracts | 0.01 |
| Grapefruit extract | |
| Cucumber extract | |
| Green Tea extract | |
| Bee Pollen extract | |
| Citrus Flower extract | |
| Chamomile extract | |
| Sea Kelp extract | |
| Lavender extract | |

EXAMPLE 5

Similar results are obtained if procedures of Examples 1-4 are repeated, except that the green marine algae component of the compositions are extracts of:

Enteromorpha adriatica
Enteromorpha ahlneriana var. roscoffensis
Enteromorpha aragoensis
Enteromorpha bayonnensis
Enteromorpha bulbosa
Enteromorpha chartacea f. minor

*Enteromorpha compressa* var. *caespitosa*
*Enteromorpha compressa* var. *abbreviata*
*Enteromorpha adriatica*
*Enteromorpha ahlneriana* var. *roscoffensis*
*Enteromorpha aragoensis*
*Enteromorpha bayonnensis*
*Enteromorpha chartacea* f. *minor*
*Enteromorpha compressa* f. *gracillis*
*Enteromorpha intestinales*
*Enteromorpha clathera*
*Enteromorpha complanata*
*Enteromorpha vulgaris*
*Enteromorpha usneoides*
*Entermorpha chlorotica*
*Ulva compressa*
*Ulva confervoides*
*Ulva conglobata* f. *densa*
*Ulva cornuta*
*Ulva covelongensis*
*Ulva crassa*
*Ulva crassimembrana*
*Ulva curvata*
*Ulva dactylifera*
*Ulva rigida*
*Ulva rotundata*
*Codium fragile*

Having disclosed the invention in such terms as to enable persons skilled in the art to understand and practice it and, having identified the presently preferred embodiments thereof, I Claim:

1. A method of treating hot flashes of a woman during peri-menopause or menopause, comprising applying to the skin of the woman experiencing hot flash onset a composition comprising a green marine algae extract of *enteromorpha compressa* in a pharmacologically acceptable liquid carrier.

2. A method of treating hot flashes of a woman during peri-menopause or menopause, comprising applying to the skin of the woman experiencing hot flash onset a composition comprising an extract of a green marine algae in a pharmacologically acceptable liquid carrier wherein the green marine algae is selected from the group consisting of *Enteromorpha adriatica, Enteromorpha ahlneriana* var. *roscoffensis, Enteromorpha aragoensis, Enteromorpha bayonnensis, Enteromorpha bulbosa, Enteromorpha chartacea* f. *minor, Enteromorpha compressa* var. *caespitosa, Enteromorpha compressa* var. *abbreviata, Enteromorpha adriatica, Enteromorpha ahlneriana* var. *roscoffensis, Enteromorpha aragoensis, Enteromorpha bayonnensis, Enteromorpha chartacea* f. *minor, Enteromorpha compressa* f. *gracillis, Enteromorpha intestinales, Enteromorpha complanata, Enteromorpha vulgaris, Enteromorpha usneoides, Enteromorpha chlorotica, Ulva compressa, Ulva confervoides, Ulva conglobata* f. *densa, Ulva cornuta, Ulva covelongensis, Ulva crassa, Ulva crassimembrana, Ulva curvata, Ulva dactylifera, Ulva rigida, Ulva rotundata, Codium fragile*, and combinations thereof.

* * * * *